United States Patent [19]

Van Dam

[11] Patent Number: 5,065,738
[45] Date of Patent: Nov. 19, 1991

[54] LARYNGOSCOPE BLADE SHEATH

[76] Inventor: David J. Van Dam, 2464 Kimberly Fair, Rochester Hills, Mich. 48309

[21] Appl. No.: 465,989

[22] Filed: Jan. 16, 1990

[51] Int. Cl.$^5$ ............................................... A61B 1/26
[52] U.S. Cl. ..................................................... 128/11
[58] Field of Search ........................ 128/10, 11, 15, 16, 128/17, 18

[56] References Cited

U.S. PATENT DOCUMENTS

| | | | |
|---|---|---|---|
| 3,426,749 | 2/1969 | Jephcott | 128/11 |
| 4,579,108 | 4/1986 | Bauman | 128/10 |
| 4,583,527 | 4/1986 | Musicant et al. | 128/11 |
| 4,834,077 | 5/1989 | Sun | 128/11 |
| 4,878,486 | 11/1989 | Slater | 128/11 |

Primary Examiner—Edward M. Coven
Assistant Examiner—Mark S. Graham
Attorney, Agent, or Firm—Dykema Gossett

[57] ABSTRACT

A laryngoscope blade sheath is pressed against the upper surface of a laryngoscope blade and adhered thereto. The sheath has a pocket that receives the tip of the laryngoscope blade and provides padding on the blade at its leading edge. The sheath also has built-up padding at areas that are adjacent the teeth when the blade with the sheath thereon is in position for orotracheal or direct nasaltracheal intubation.

10 Claims, 2 Drawing Sheets

LARYNGOSCOPE BLADE SHEATH

FIELD OF THE INVENTION

The present invention relates to the laryngoscope, which is used in the technique of orotracheal or direct nasaltracheal intubation. More particularly, the present invention relates to a disposable sheath as a protective covering on a laryngoscope blade, to protect a patient's mouth and throat. Still more particularly, the present invention relates to a laryngoscope blade sheath having adequate padding to protect a patient's teeth, tongue, fauces, pharynx, and epiglottis, when the laryngoscope blade is inserted in the patient's mouth.

BACKGROUND OF THE INVENTION

During a specific surgical operation or some other procedure requiring oral or nasal endotracheal intubation, one or more endotracheal tubes are inserted into a patient via the mouth and throat or nose and throat of the patient, to facilitate positive pressure ventilation to and from the patient's lungs during the surgery. The technique of orotracheal or direct nasaltracheal intubation involves sighting the insertion of the endotracheal tube into the throat of an anesthesized patient. A variety of equipment may be used for this technique, but always including a proper sized endotracheal tube or tubes, a functioning laryngoscope, and appropriate anesthetic drugs and neuromuscular blockers. After the tube is inserted there must be, of course, facilities to provide the positive pressure, oxygen ventilation.

Training and experience contribute to making the technique safe, effective, and atraumatic. For example, a safe approach to a surgical procedure involves first providing the patient with a barbituate and a skeletal muscle relaxant before initiating laryngoscopy. Then the head, neck, and shoulders of the patient must be positioned so that the oral, pharyngeal, and laryngeal axes are aligned. Finally, the laryngoscope is inserted, preferably with the laryngoscopist's left hand—without regard to whether the laryngoscopist is right or left handed—on the right side of the patient's mouth to avoid the incisor teeth and to deflect the tongue away from the lumen of the laryngoscope blade. The laryngoscopist sights the epiglottis above the base of the tongue and, according to the type of laryngoscope blade used, manipulates the instrument to expose the glottis opening.

There are many types of laryngoscope blades, each characterized by the blade curvature or lack thereof, the point of such curvature if the blade is curved, and the flange structure of the blade. Three types of blades are most prominently used. A first type of blade, characterized as a curved blade, is known in the art as the Macintosh blade. This type of blade is advanced into the space between the base of the tongue and the pharyngeal surface of the epiglottis. Forward and upward movement of this blade stretches the hypoepiglottic ligament to cause the epiglottis to move upward to expose the glottic opening. Two other types of prominently used blades are the straight blade, known as the Jackson or Wisconsin blade, and the straight blade with a curved tip, known in the art as the Miller blade. The tip of these blades are passed beneath the laryngeal surface of the epiglottis and moved upwardly to elevate the epiglottis, thereby exposing the glottic opening.

During insertion of the laryngoscope, care must be taken to avoid pressure on the teeth and gums of the patient. Care must also be taken to avoid traumatizing the oral mucosa and to avoid bruising the epiglottis. By using a gentle technique for inserting the laryngoscope, the laryngoscopist might lessen the possibility of such trauma. But choice of instrumentation might also lessen trauma. For example, less trauma to the teeth is associated with a curved blade, and because the curved blade should not touch the epiglottis, there is less bruising of the epiglottis associated with use of the curved blade. Another trauma lessening instrument is a protective shield that might be placed over the maxillary incisors.

These methods and instrumentation have limited advantage. No matter how gentle the insertion, the manipulation to expose the glottic opening is an invasive technique whereby the hard edge of the blade scrapes against the oral mucosa when manipulated to open the glottis. Whatever advantages are associated with use of the curved blade, there are also advantages to use of the straight blade, and its choice is often the result of personal preference by the laryngoscopist. Even the protected shield has limited advantage, as it only protects the teeth and not the tongue and oral mucosa.

OBJECTS OF THE INVENTION

Thus, there is a need for a means of reducing still further the trauma to which all of the mouth and throat are exposed during the technique of oral tracheal intubation. One object of the present invention is to provide a device to protect the teeth, tongue, and oral mucosa from the blade of a laryngoscope during orotracheal or direct nasaltracheal intubation.

Another object of the present invention is to provide a device to protect the teeth, tongue and oral mucosa for all curved, straight and partially curved types of laryngoscope blades.

Still another object of the present invention is to provide a method of carrying out the technique of orotracheal or direct nasaltracheal intubation whereby the teeth, tongue, and oral mucosa are protected.

These and other objects will be better understood when the device and method of the present invention are described in the detail of the preferred embodiment and particularly pointed out and distinctly claimed in the claims.

SUMMARY OF THE INVENTION

To summarize the preferred embodiment, a sheath is adapted to fit on the blade of a laryngoscope to protect the teeth, tongue and oral mucosa of a patient during orotracheal or direct nasaltracheal intubation. The laryngoscope, well known to those of ordinary skill in the art, comprises a blade, a handle, and a lamp. The handle houses one or more batteries as a power source for the lamp. The lamp is used to sight the glottic opening for insertion of an endotracheal tube into the opening.

The blade of the laryngoscope is characterized as longitudinal and as having a tip that is blunted to reduce invasive scraping of the mucosa when the blade is introduced into a patient's mouth. At the other end of a blade, opposite the tip, the blade connects to the handle. The connection may be in the nature of the blade being integrally affixed to the handle, or the blade being permanently affixed to the handle, or the blade being detachably attached to the handle. As a preferred embodiment, a short pivot arm extends perpendicularly from the longitudinal axis of the blade. This pivot arm releasably connects in pivotal articulation with the handle.

The blade may be arcuate, generally curving transversely from one edge of the blade to a flange that extends inwardly of the curvature, along a cord of the curve. A blade having this transverse curvature is used to roll the tongue of a patient out of the way and allow the laryngoscopist to sight under the arc of the blade. The blade also may curve longitudinally, or may be straight, or may be a combination of curvature and straight configuration along its longitudinal axis, according to conventional blades found in the art. Other types of blades, for example the Macintosh blade, are not transversely arcuate but may nevertheless bend into a perpendicular portion from which it bends again perpendicularly into a flange.

The invention itself is a flat, planar, pliable sheath that is shaped as a flattened laryngoscope blade. Accordingly, the sheath has a tip end corresponding to the tip of a laryngoscope blade, and a butt end corresponding to the end of the blade proximate the pivot arm which connects to the handle. The sheath also is characterized as having an exposed surface and an adhesive surface. On the exposed surface, generally from the butt end of the sheath to generally the middle of the sheath, the sheath has a thicker cross-section than the rest of the sheath. This cross-section provides padding for the incisors of the patient when the laryngoscope blade is in the patient's mouth.

Preferably, two thickened cross-sections are provided. One of these thickened padded portions is situated generally along the edge of the sheath corresponding to the edge of the blade terminating in a flange. The other thickened portion is more proximate the opposite edge of the sheath and has a width extending more toward the middle of the sheath. The thinner cross-section between the two padded sections allows for the sheath to be more pliable in bending with the transverse curvature of the blade. The tip of the sheath also has a thickened pad on both the exposed surface and the adhesive surface of the sheath. A pocket is provided on the adhesive surface of the sheath for sliding the tip of the laryngoscope blade thereinto. Substantially all of the adhesive surface of the sheath, except for the padded portion having the pocket, is provided with a pressure sensitive adhesive. This adhesive may be protected by a waxed film that may be peeled off to expose the adhesive for application.

The sheath is made of a soft, pliable thermoplastic foam, for example, polyurethane, that may be isolated in packaging to provide a clean sheath for insertion into the mouth. The material only has to be durable enough for a one time use of the sheath.

In use, the sheath is taken from its isolation packaging under sterile conditions. The tip of the laryngoscope blade is inserted into the pocket in the tip of the sheath. The adhesive protecting film is removed to expose the adhesive and the adhesive surface of the sheath is pressed against the upper surface of the laryngoscope blade. Care is taken to make sure that the sheath intimately engages the blade according to both its transverse and longitudinal curvature.

During orotracheal or direct nasaltracheal intubation, the laryngoscope with the protective blade sheath adhered to the laryngoscope blade is inserted into the mouth. The padded portions of the blade protect the teeth and mucus membrane from the hard surface and sharp edges of the laryngoscope blade as the blade is positioned within the mouth.

BRIEF DESCRIPTION OF THE DRAWINGS

The invention can be more readily understood by reference to the accompanying drawings figures, in which.

DESCRIPTION OF THE PREFERRED EMBODIMENT

Figure 1:
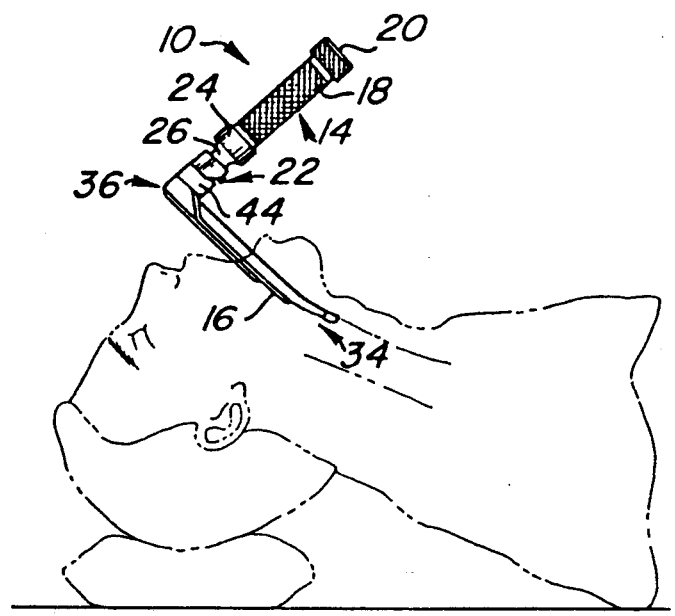
FIG. 1 depicts a technique of orotracheal or direct nasaltracheal intubation, showing the orientation of a laryngoscope when the blade of the laryngoscope is inserted into the mouth of a patient, who is shown in phantom.
Figure 2:
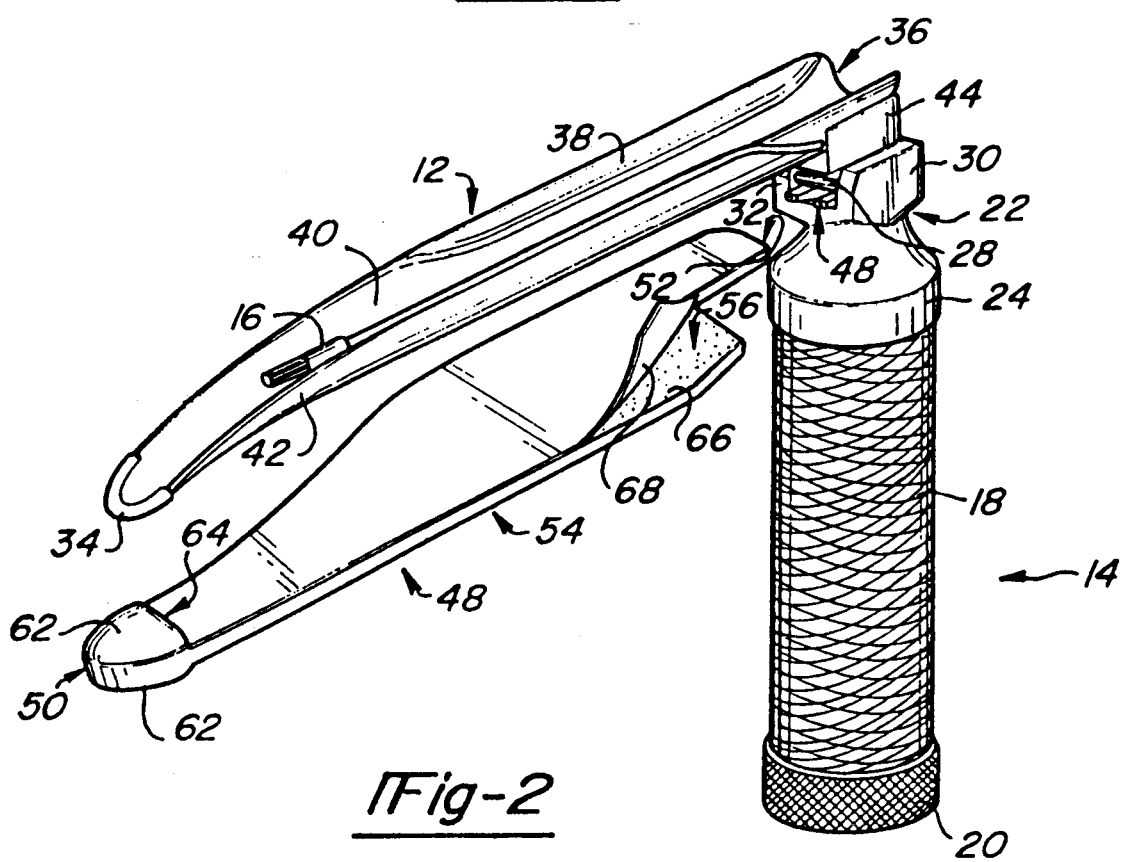
FIG. 2 depicts a laryngoscope, in perspective, with a protected sheath according to the invention, the sheath with protective film over its adhesive backing being shown diagrammatically below the blade of the laryngoscope and being shown in the orientation that the sheath would have prior to being pressed against the upper surface of the blade.
Figure 3:
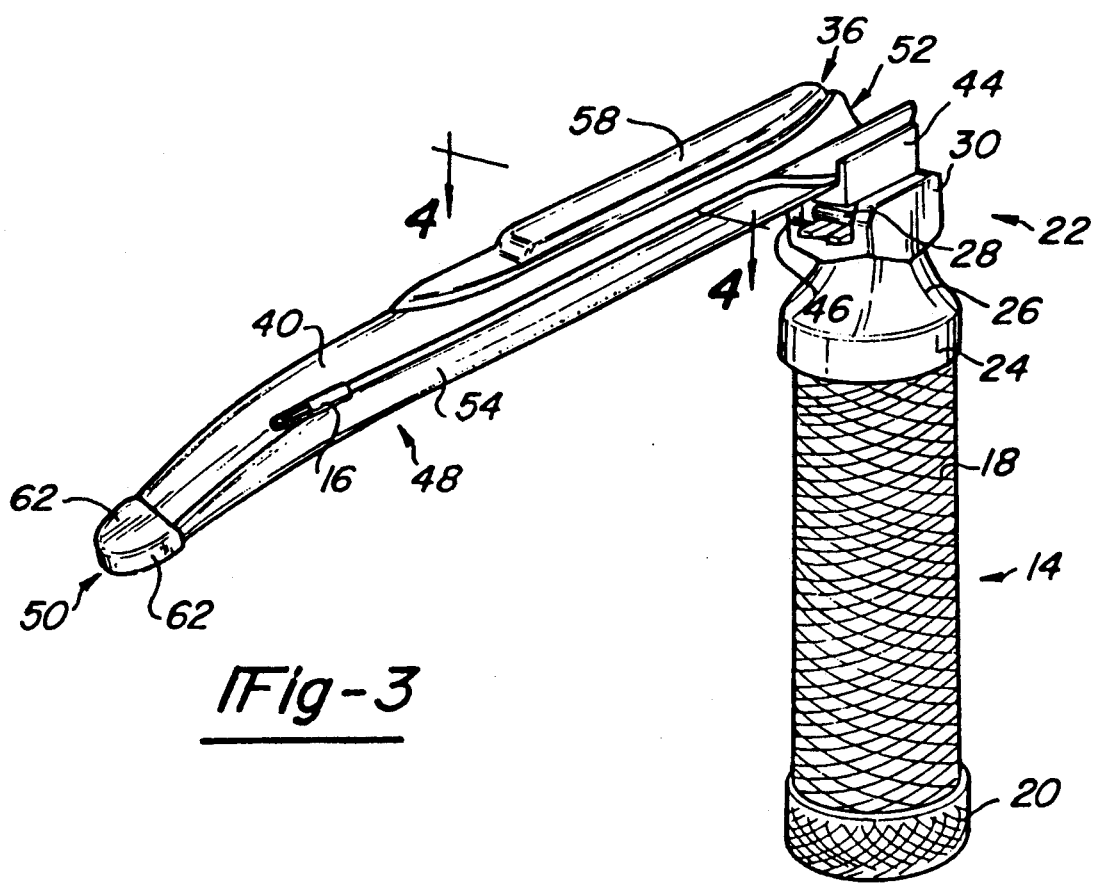
FIG. 3 depicts a laryngoscope in perspective as shown in FIG. 2 with the protective sheath in place on the blade.

Referring to the figures, in which the same reference numerals are associated with the same parts throughout, the laryngoscope is generally referred to by the reference numeral 10. Particularly as shown in FIG. 2, the laryngoscope 10 generally comprises a blade 12, a handle 14 and a lamp 16. As is shown in FIG. 1, the orientation of the laryngoscope 10 is such that the handle extends generally upwardly. This orientation will determine the convention to be used in this description of the preferred embodiment to relate the parts of the layngoscope. Accordingly, the free end of the handle will be considered upwards of the rest of the laryngoscope 10.

A cap 20 is screwed onto the free end of the handle. The handle 14 houses one or more batteries, as an example, two "C" batteries (not shown). The batteries are insertable into a tubular housing 18 of the handle 14, when the cap 20 is unscrewed and taken off to access a hollow battery chamber of the handle 14. A U-section support 22 on the opposite end of handle 14 provides a pivotal support for blade 12, as will be explained below. A collar 24 is rigidly attached to the housing 18 and is integrally connected to the support 22 via an integral neck 26. The support 22 is provided with a pivot rod 28 spanning the flanges 30, 32 of the U-section support 22.

Lamp 16 extends longitudinally between a blade tip 34 and a blade handle end 36. The blade is electrically connected to the handle, although the connection may be via the blade 12, particularly with fiberoptic blades 12. Lamp light provided to sight the glottic opening is more intense with fiberoptic technology.

Blade 12 may be one of a variety of blades available for the laryngoscopes 10. The most conventional of the variety of blades 16 are the curved, Macintosh blade, the straight, Jackson or Wisconsin blade, and the straight, with a curved portion proximate the tip, Miller blade. The laryngoscopist has a choice of which blade to use, and the choice is most often a personal preference. The blades may also be of different sizes that are adapted for specialty needs, for example, sizes for infants and children.

The blade 12 must be made of a material that is durable and easy to clean. Conventionally, stainless steel is used. Fiberoptic blades have the advantage that they require no internal wiring for the lamp 16.

Figure 4:
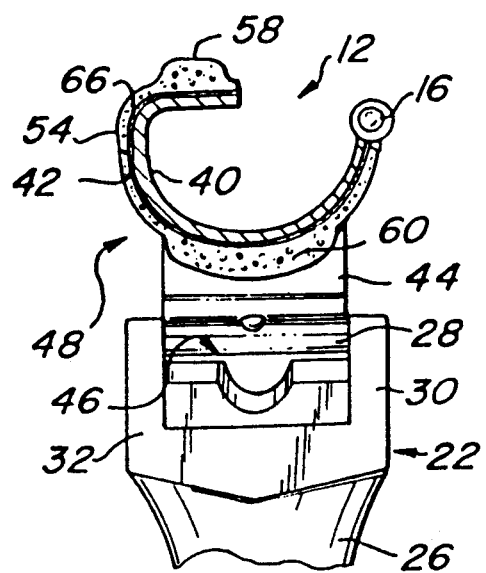
FIG. 4 depicts a cross-sectional view in the direction of arrows 4—4 of FIG. 3.

The blade 12 of the preferred embodiment is arcuate, generally curving transversely from one edge of the blade 12 to a flange 38 that extends inwardly of the curvature, along a cord of the curve, all of which is shown in FIG. 4. The blade 12 is used to roll the tongue of a patient out of the way and allow the laryngoscopist to sight under the arc of the blade 12. The blade 12 also curves longitudinally, but other available blades known to those of ordinary skill in the art are straight or a combination of curvature and straight configuration along its longitudinal axis. Some of these other types of blades are not transversely arcuate. For example, the Macintosh blade is straight in transverse cross-section and bends into a perpendicular portion from which it bends again perpendicularly into a flange. The upper flange 38 is eliminated in some specialty blades for patients with restricted mouth openings.

The tip 34 of blade 12 is rounded or blunted with a structural lip so that, when the blade 12 is slid along the oral mucosa is with the tip 34 leading, there is some limited protection against the edge of the blade 12 scraping the oral mucosa. The blade 12 has a undersurface 40 and an upper surface 42. According to the structure of the blade 12, the upper surface 42 is generally convex while the undersurface 40 is generally concave.

At the other end of the blade 12, proximate the handle end 36, the blade 12 connects to the handle 14. The connection may be in the nature of the blade 12 being integrally affixed to the handle 14, or the blade 12 being permanently affixed to the handle 14, or in the case of the preferred embodiment, the blade 12 being detachably attached to the handle 14. As the preferred embodiment, a short pivot arm 44 extends perpendicularly from the upper surface 42. Pivot arm 44, which provides a fulcrum for blade 12, is shown more particularly in FIG. 4. Arm 44 has a slot 46 which effects a hook configuration so that arm 44 hooks around the pivot rod 28 of handle 14. U-section 22 has releasable stops to stop pivot arm 44 in at least two positions and thus present blade 12 in at least two positions. One position in which blade 12 is presented is generally perpendicular to handle 14; the other in which blade is presented is generally parallel and folded into juxtaposition with handle 14. Accordingly, blade 12 pivots between its two stopped positions. The folding position is for non-use and for unhooking the blade from the handle 14. The generally perpendicular position is the position in which the laryngoscope 10 is used for orotracheal or direct nasaltracheal intubation. When in the generally perpendicular position, electrical contact is made with the batteries in handle 14, to turn on the lamp 16.

The present invention is adapted for use with laryngoscopes 10 of a structure just described, which structure is known to those of ordinary skill in the art. The invention comprises a sheath 48 that is generally a flat, planar, pliable sheet of plastic material. The present invention also includes a laryngoscope of the technology described with the improvement of sheath 48.

Preferably, sheath 48 is shaped generally as the shape as a laryngoscope blade, for example blade 12, if the blade 12 were flattened out as a sheet. According to its correspondence with the blade 12, the sheath 48 has a tip end 50 corresponding to the tip of a laryngoscope blade, and a butt end 52 corresponding to the blade pivot end 36 of the blade 14, proximate the pivot arm 28 which hooks onto the handle 14. The sheath 48 also is characterized as having an exposed surface 54, which is exposed when the sheath 48 is bonded by means adhering the sheath 48 to the upper surface 42 of the blade 36. Preferably, for certain additional advantages that will be explained, the means for adhering the sheath 48 to the upper surface 42 allows the sheath 48 to be peeled off of uppersurface 42 of blade 12 to expose an adhesive surface 56 of the sheath 48 opposite the exposed surface 54 of the sheath 48.

On the exposed surface 54, generally from the butt end 52 of the sheath 48 to generally the middle of the sheath 48, the sheath 48 has at least one pad, for example a combination of a flange pad 58 and an upper surface pad 60, that has a thicker cross-section than the rest of the sheath 48. This cross-section provides padding for the incisors of the patient when the laryngoscope blade is in the patient's mouth as shown in FIG. 1. Preferably, two thickened cross-sections, the flange pad 58 and the upper surface pad 60, are provided. The flange pad 58 is situated generally along an edge portion of the sheath 48 corresponding to the flange 38.

The other thickened portion, the upper surface pad 60, is proximate the opposite edge portion of the sheath 48, corresponding to the upper surface of the blade 12 arcing most protrusively in a direction that is generally parallel to the direction in which the handle extends. According to the preferred orientation of the laryngoscope when placed in the patient's mouth, this upper surface pad 60 is most proximate the upper incisors of the patient's mouth. The upper surface pad 60 has a width extending more toward the middle of the sheath 48. The thinner cross-section between the two padded sections 58 and 60 which is the generally uniform thickness of the sheath 48 allows for the sheath 48 to be more pliable in bending with the transverse curvature of the blade 12.

The tip end 50 of the sheath 48 also has a thickened pad 62 on both the exposed surface 54 and the adhesive surface 56 of the sheath 48. A slot into a pocket 64 is provided on the adhesive surface 56 of the sheath 48 for sliding the tip 34 of the laryngoscope blade thereinto, thus capturing the tip 34 and securing the tip end 50 of the sheath 48 to the tip 34 to provide protection to the mouth, teeth and throat from the much harder, albeit blunted tip 34.

Substantially all of the adhesive surface 56 of the sheath 48, except for the tip end pad 62 having the pocket 64, is provided with a pressure sensitive adhesive 66. This adhesive may be protected by a waxed film 68 that may be peeled off to expose the adhesive for applying the sheath 48 to the upper surface 42 of blade 12.

The sheath is preferably made of a soft, pliable thermoplastic foam, for example, polyurethane, that may be isolated in packaging to provide a clean sheath 48 for insertion into the mouth. The material only has to be durable enough for a one time use of the sheath 48. Preferably, the sheath has a thickness approximately 0.125 inches with the padded portions being approximately 0.25 inches. The tip end being padded on both sides of the sheath would be approximately 0.5 inches.

In use, the sheath 48 is taken from its isolation packaging. The tip 34 of the laryngoscope blade 12 is inserted into the pocket 64 in the tip end 62 of the sheath 48. The adhesive protecting film 68 is removed to expose the adhesive 66 and the adhesive side 56 of the sheath 48 is pressed against the upper surface 42 of the laryngoscope blade. Care is taken to make sure that the sheath 48 intimately engages the blade according to both its transverse and longitudinal curvature.

During orotracheal or direct nasaltracheal intubation, the laryngoscope 10 with the protective blade sheath 48 adhered to the laryngoscope blade 12 is inserted into the patient's mouth as shown in FIG. 1. The padded portions of the sheath 48 on the blade 12 protect the teeth and mucus membrane from the hard surface and sharp edges of the laryngoscope blade 12 as the blade 12 is positioned within the patient's mouth. After use of the laryngoscope 10, the sheath 48 may be pealed from the upper surface 42 of the blade 12 before the blade 12 is cleaned. The used sheath 48 may be discarded.

I claim:

1. A laryngoscope blade sheath for covering at least one surface side of a laryngo-scope blade having a tip, a pivot end, opposite transverse edges, an upper surface, and an undersurface, and being transversely arcuate, generally curving from one edge of the blade to the other, the sheath comprising:

a substantially flat, planar, pliable sheet having a generally uniform thickness over substantial portions thereof and an added thickness over at least one portion thereof, said sheet having a tip end, a butt end, and an exposed surface, said exposed surface being contoured according to said at least one portion of said sheet having additional thickness to said uniform thickness;

means disposed at said tip end for capturing the tip of a laryngoscope blade; and an adhesive surface for adhering said sheath to the upper surface of a laryngoscope blade white adapted for leaving the undersurface of the laryngoscope blade substantially uncovered by said blade sheath.

2. The sheath described in claim 3 wherein said adhesive surface opposite said exposed surface of said sheath comprises pressure adhesive on said adhesive surface of said sheath.

3. The sheath described in claim 1, wherein said means of capturing the tip of said laryngoscope blade is a pocket located in the tip end of said sheath.

4. The sheath described in claim 3, wherein said pocket opens through a slot in said tip end, said slot being accessible from the adhesive surface of said sheath, whereby said tip of said laryngoscope blade may be slid into said slot to be captured by said pocket and secured to said blade thereby.

5. The sheath described in claim 3 wherein said added thickness is over substantially all of said tip end.

6. The sheath described in claim 1 wherein said portion having additional thickness is proximate the butt end of said sheath.

7. The sheath described in claim 6 wherein at least one other portion of said sheath has added thickness, said at least one other portion being over substantially all of said tip end.

8. A method of performing orotracheal or direct nasaltracheal intubation using a laryngoscope having a butt and a blade connected to said handle, said blade including a tip end remote from said handle, a handle end adjacent said handle, and upper surface facing substantially in said first direction, a leading edge and an undersurface facing substantially opposite said upper surface, said laryngoscope used to introduce an endotracheal tube into the mouth of a patient and to insert the endotracheal tube by direct vision into the glottic opening of the patient, the method comprising the steps of:

preparing the blade by providing resilient padding to cover the upper surface and leading edge of the blade, while leaving the undersurface of the blade substantially uncovered;

introducing the blade into the mouth of the patient with the padding on the laryngoscope blade padding the leading edge of the blade;

manipulating the blade to expose the glottic opening; and, discarding the padding after orotracheal or direct nasaltracheal intubation and before the laryngoscope blade is cleaned.

9. The method of claim 8, wherein the step of preparing the blade includes providing additional resilient padding proximate the handle end of the blade and the step of introducing the laryngoscope into the mouth of the patient includes the substep of resting the additional padding against the lower incisors of the patient.

10. The method of claim 8, wherein the step of preparing the blade includes attaching the resilient padding to the upper surface of the blade, the padding being in the form of a first sheath having a substantially planar adhesive side that has an pressure sensitive adhesive thereon for attaching the sheath to the blade, the sheath being shaped generally as the shape of the blade to substantially cover the upper surface of the blade and the tip of the blade, and wherein said step of discarding the padding includes detaching said first sheath from said upper surface of said blade, the method further comprising attaching a second sheath to said upper surface after said first sheath is detached.

* * * * *